United States Patent

Stashkiw et al.

[11] Patent Number: 5,847,568
[45] Date of Patent: Dec. 8, 1998

[54] MOISTURE SENSOR AND IRRIGATION CONTROL SYSTEM

[76] Inventors: Robert M. Stashkiw; Dean L. Cramer, both of 22502 Petra, Mission Viejo, Calif. 92692

[21] Appl. No.: 868,497

[22] Filed: Jun. 3, 1997

[51] Int. Cl.[6] .................. G01N 27/07; A01G 25/16
[52] U.S. Cl. .................. 324/696; 324/694; 137/78.3; 239/63; 73/73
[58] Field of Search .................. 324/664, 689, 324/690, 694, 696, 713, 717, 724; 73/73, 304 C; 340/604; 137/78.2, 78.3, 624.11, 624.12; 239/64, 70, 63

[56] References Cited

U.S. PATENT DOCUMENTS

| | | | |
|---|---|---|---|
| 3,224,676 | 12/1965 | Rauchwerger | 239/64 |
| 3,553,481 | 1/1971 | Hansenbeck | 239/63 |
| 4,137,931 | 2/1979 | Hasenbeck | 137/78.3 |
| 4,216,789 | 8/1980 | Hasenbeck | 137/78.3 |
| 4,399,699 | 8/1983 | Fujishiro | 73/304 C |
| 4,548,225 | 10/1985 | Busalacchi | 137/78.3 |
| 4,693,419 | 9/1987 | Weintraub et al. | 137/78.3 |
| 4,796,654 | 1/1989 | Simpson | 137/78.3 |
| 4,850,386 | 7/1989 | Bireley | 137/78.3 |
| 4,875,498 | 10/1989 | Andrews et al. | 137/78.3 |
| 4,892,213 | 1/1990 | Mason, Jr. . | |
| 4,936,333 | 6/1990 | Bireley | 137/78.3 |
| 4,993,640 | 2/1991 | Baugh | 137/78.3 |
| 5,060,859 | 10/1991 | Bancroft | 239/64 |
| 5,148,985 | 9/1992 | Bamcroft | 239/64 |
| 5,375,617 | 12/1994 | Young | 137/78.3 |
| 5,445,176 | 8/1995 | Goff | 137/78.3 |
| 5,546,974 | 8/1996 | Bireley | 137/78.3 |

Primary Examiner—Diep N. Do
Attorney, Agent, or Firm—Knobbe, Martens, Olson & Bear LLP

[57] ABSTRACT

Disclosed is a control system for regulating irrigation to an area of land. The irrigation control system includes a control unit, a photosensor, a timer or controller and a moisture probe for sensing the moisture level in the area to be watered. The control unit is configured to disable power to the system if the moisture level in the area of land exceeds a predetermined level as measured by the moisture probe, which is buried in the watering area. In a preferred embodiment, the moisture probe consists of two electrode plates, preferably manufactured of high purity copper, that are oriented parallel to one another. The electrode plates each have a predetermined length and thickness and are separated by a predetermined distance, each of which are configured to optimize the moisture detecting characteristics of the probe. The control unit applies an electrical potential across the electrode plates such that the resistance of the soil located therebetween varies as a function of moisture content. The control unit measures the soil resistance to thereby determine the moisture content of the soil.

26 Claims, 7 Drawing Sheets

MOISTURE SENSOR AND IRRIGATION CONTROL SYSTEM

BACKGROUND OF THE INVENTION

1. Field of the Invention

The present invention relates to a sprinkler control system. More particularly, the present invention relates to a moisture probe that controls a sprinkler system based upon the soil moisture content of an area to be watered.

2. Description of the Related Art

Water conservation is an area of growing concern in today's society. As the population grows, the demand for and consumption of water is increasing, resulting in a general decrease in water supplies in many geographical areas. In response to water shortages, many state and local governments have issued guidelines and regulations regarding water consumption in order to promote the conservation and efficient use of available water supplies. Such regulations and guidelines often relate to the amounts of water that may be used for certain activities, such as for land irrigation.

Landscape irrigation accounts for a large percentage of the water that is used by businesses and individuals such as homeowners. Unfortunately, studies have shown that homeowners consistently apply their lawn with at least twice as much water as the lawn actually requires for healthy growth. This results in the inefficient use of available water supplies, as well as water bills that are unnecessarily high.

One reason that many homeowners commonly over-water their lawns is that such homeowners are often unaware of the actual irrigation needs of their particular lawn. Given the wide range of lawn and soil types, many homeowners have neither the knowledge nor the know how relating to the irrigation requirements of a particular lawn. Moreover, even if equipped with such knowledge, it would likely be inconvenient for a homeowner to consistently check the moisture level in a lawn or garden area prior to watering.

Instead, homeowners often prefer the convenience of attaching a controller or timer switch to their irrigation system. A typical timer switch opens the sprinkler valves for a specific amount of time each day. While such timers may be convenient, they are also inefficient in that they deliver water based only upon the time of day, regardless of whether the moisture level is already sufficient for the particular irrigation needs of the lawn, such as during rain. Hence, the use of a timer often results in the unnecessary watering of a lawn or garden.

Some homeowners may choose to use moisture probes, which are devices which measure the moisture level in an area of land and activate the irrigation system if the moisture level is low. However, current moisture probes do not exhibit optimal water-detecting characteristics. Current soil moisture probes react differently to various types of soil, thus requiring a user to adjust the probe depending on the type of soil where moisture is being measured. Furthermore, current soil probes are sensitive to placement or orientation of the probe within the soil, so that if the probe is not positioned correctly, the probe performs at a reduced level, resulting in over-watering or under-watering of a land area.

There is therefore a need for a water sprinkler system which is highly responsive to the moisture level for various lawn and soil types. The system should be responsive to small moisture changes that occur over a range of soil types and should be configured so as not to interfere with natural dispersion and flow of ground moisture.

SUMMARY OF THE INVENTION

The above-identified needs are satisfied by the present invention. In one aspect of the invention, there is disclosed a soil probe system configured to measure the level of moisture in a watering area. The soil probe system includes a moisture probe including a first electrode having a substantially elongated, flat shape and having a length, a width, and a thickness. A second electrode has a length, a width, and a thickness that are each substantially identical to the length, width, and thickness of the first electrode. The second electrode is oriented substantially aligned and parallel to the first electrode. The first electrode is spaced apart from the second electrode by a predetermined distance. Spacers removably connected to the first and second electrodes maintain the orientation of the first electrode relative to the second electrode. The system further includes a source of electrical power connected to the first and second electrode for applying an electrical potential to the first and second electrode and a control unit for measuring the electrical potential between the first and second electrode. The control unit is configured to disable a flow of electrical power from the source of electrical power to a water valve if the electrical potential is below a predetermined value.

In another aspect of the invention, there is disclosed a method for controlling water distribution to soil, comprising the steps of forming a moisture sensor by placing first and second substantially flat and substantially parallel, elongated plates a predetermined distance apart and interposing at least one insulating member between the plates to position those plates relative to each other, the plates having a predetermined width, length and thickness, placing the moisture sensor in the soil so the length of the plates is substantially parallel to the ground, applying a direct current voltage to one of the plates and monitoring the other plate for an electric signal, and comparing any such signal with a predetermined value to determine whether to apply water to the soil in which the sensor is placed.

In yet another aspect of the invention, there is disclosed a watering system for watering a series of watering zones comprising a power supply for supplying power along a power path. A first soil probe system is located along the power path. The first soil probe system includes a first water valve connected to a first sprinkler, a first moisture probe configured to measure the moisture level in a first watering zone, and a first control unit communicating with the first moisture probe and the first water valve. The first control unit is configured to close the first water valve if the moisture level is below a predetermined level. A second soil probe system is located along the power path and includes a second water valve connected to a second sprinkler, a second moisture probe configured to measure the moisture level in a second watering zone, and a second control unit configured to close the second water valve if the moisture level in the second watering zone is below the predetermined level. A relay is located in the power path between the power supply and the second soil probe system. The relay is controlled by the first control unit to allow power to flow across the relay when the moisture level in the first watering zone is greater or equal to the predetermined level, and to inhibit power from passing across the relay when the moisture level in the first watering zone less than the predetermined level.

These and other features of the invention will now be described with reference to the drawings of the preferred embodiment of the moisture sensor and irrigation control system. The illustrations are intended to illustrate, but not to limit the invention.

DETAILED DESCRIPTION OF THE PREFERRED EMBODIMENT

Figure 1:
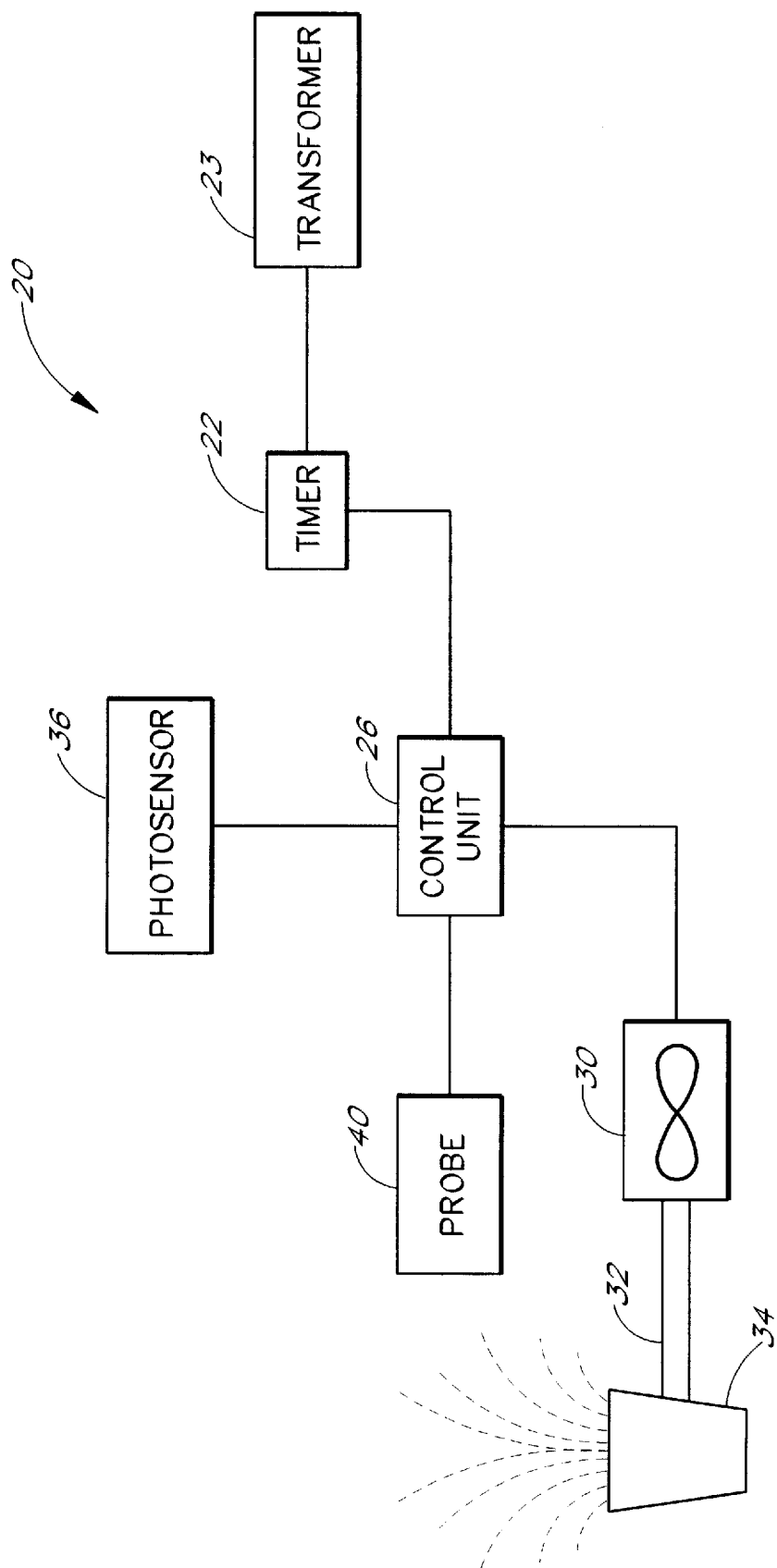
FIG. 1 schematically illustrates the components of the sprinkler system of the present invention.

FIG. 1 schematically illustrates an irrigation system 20 configured in accordance with a preferred embodiment of the present invention. One embodiment of the irrigation system 20 consists of a number of components, including a timer 22, a control unit 26, at least one sprinkler valve 30 which is connected to a plurality of irrigating heads 34, and a moisture sensor or probe 40 for detecting the level of moisture in a watering zone in accordance with the present invention. As used herein, the term "watering zone" refers to an area of land that is to be watered using the irrigation system 20. Any wide variety of plant life may be located in the watering zone, such as, for example, lawn, trees, shrubbery or gardens. The watering zone may be located on a homeowner's yard, an industrial landscape, a park, farm land or any other area of land that is irrigated.

As discussed, the irrigation system 20 may include an electronic timer 22 which is connected to a source of electrical power such as a standard 110 VAC power outlet (not shown). A VAC transformer 23 may be used to reduce the voltage to a suitable level. The electronic timer 22 preferably includes a set of switches (not shown) which an operator may set to energize the irrigation system 20 for a desired length of time based upon the hours of the day and the day of the week or month. Any type of standard, prior art electrical sprinkler timer may be used. The timer 22 need not be included in the irrigation system 20 of the present invention. Alternatively, an operator may directly connect the irrigation system 20 to a source of electrical power (not shown) for continuous energization of the irrigation system 20, with a transformer being used when appropriate.

As illustrated in FIG. 1, the irrigation system 20 further includes a control unit 26 which is interposed along an electrical circuit between the timer 22 and the other components of the irrigation system 20. The control unit 26 controls and monitors a number of functions of the irrigation system 20, as described in detail below. Preferably, the control unit 26 is electrically connected to the timer 22 so that the control unit 26 acts as a conduit to route electrical power to the rest of the components of the irrigation system 20. In a preferred embodiment, the control unit 26 includes a transformer 23 that converts the 110 VAC electrical current received from the timer 20 into a 24 VAC that is received by the timer 22 and delivered to the solenoid at the sprinkler valve 30. Depending on the power source, other suitable transformers could be used. The transformer 23 may be external to the control unit 26. The control unit 26 converts the incoming 24 VAC to DC for internal use, applies a voltage for external use at the moisture probe 40, and control circuity decides whether or not to pass the 24-VAC to the sprinkler valve 30. The probe is an impedance circuit. Advantageously, the control unit 26 includes a converter (not shown) for converting the 24 VAC current into a 1.5 DC current that the control unit 26 supplies to the moisture probe 40, as described in detail below.

As shown in FIG. 1, the control unit 26 is electrically connected to an electronically-controlled sprinkler valve 30, which is connected to a source of pressurized water (not shown). The sprinkler valve 30 may be any type of electronically-controlled valve, but advantageously is one which opens in response to receiving an electrical current of a pre-determined voltage. Preferably, the valve 30 is a standard, electronically-controlled 24 VAC anti-siphon solenoid valve.

Referring to FIG. 1, the valve 30 is connected to, and controls, the supply of water to at least one water conduit 32, so that when the valve 30 opens in response to an electrical current water flows from the pressurized water source into the water conduit 32 for distribution to the watering zone. The water conduit 32 may be any type of device known to those skilled in the art for transporting the flow of water, such as, for example, plastic or metal pipe, hose, etc. The water conduit 32 may be disposed either above or below ground. Although the irrigation system 20 is illustrated in FIG. 1 as having a single valve 30 connected to the water conduit 32, it will be appreciated that any number of valve and water conduit combinations may be used with the present invention. Preferably though, there is one valve 30 and one photosensor for each watering zone.

As shown in FIG. 1, the water conduit 32 routes a flow of water to an irrigation head 34 for dispersing water over a predetermined watering zone. Preferably, the water conduit 32 connects to a plurality of irrigation heads 34 which are distributed over the watering zone. The irrigation heads are advantageously arranged to uniformly disperse water over the entire watering zone, which may result in overlapping of the watering range of some of the irrigation heads 34. The present invention may use any wide variety of irrigation heads 34 for dispersing water over the land zone such as, for example, spray heads, drip delivery heads, a surface flooding head, or any combination thereof.

As shown in FIG. 1, the preferred embodiment of the irrigation system 20 further includes a photosensor 36 that is electrically connected to the control unit 26. The photosensor 36 is configured to detect the level of light in the ambient vicinity of the control unit 26. Preferably, the photosensor 36 contains a switch that may be set by an operator to disable the flow of electrical energy to the irrigation system 20 if the light exceeds a pre-determined level. The photosensor 36 may be used on all above ground valve configurations where, when the light exceeds a pre-determined level, the control unit 26 disconnects the 24-VAC electrical power to anti-siphon valve 30. In this manner, the operator may set the irrigation system 20 so that it operates only when light is low, such as at night, regardless of the particular time of day. The photosensor may be any type of prior art, light detecting apparatus known to those skilled in the art. Although the photosensor 36 is illustrated as being separate from the control unit 26, it will be appreciated that the photosensor 36 is optional, and may or many not be housed within the control unit 26. A control unit 26 located underground does not require a photosensor 36 as light levels are not necessary for usage, but a photosensor 36 may be used even if the control unit 26 is located underground if that is advantageous.

As shown in FIG. 1, the irrigation system 20 further includes the moisture probe 40, which is buried underground in the watering zone and electrically connected to the control unit 26. During operation, the moisture probe 40 detects the moisture level within the watering zone when the control unit supplies an electrical potential to the probe. In response to the electrical potential, the moisture probe sends an electrical signal to the control unit 26 in accordance with the amount of moisture in the soil adjacent the probe, as described in detail below. The control unit 26 evaluates the electrical signal and enables or disables electrical power to the valves 30 if the moisture level is below or above a predetermined threshold.

Figure 2:
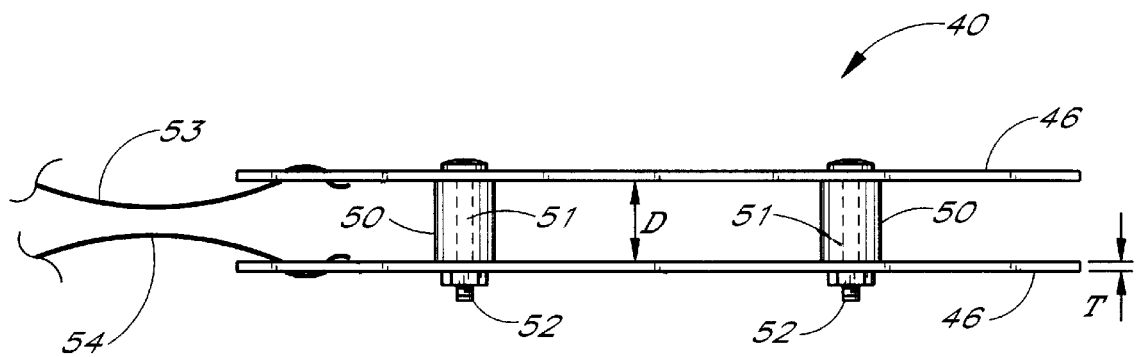
FIG. 2 is a top view of a first embodiment of a moisture probe that is used in the sprinkler system of the present invention.
Figure 3:
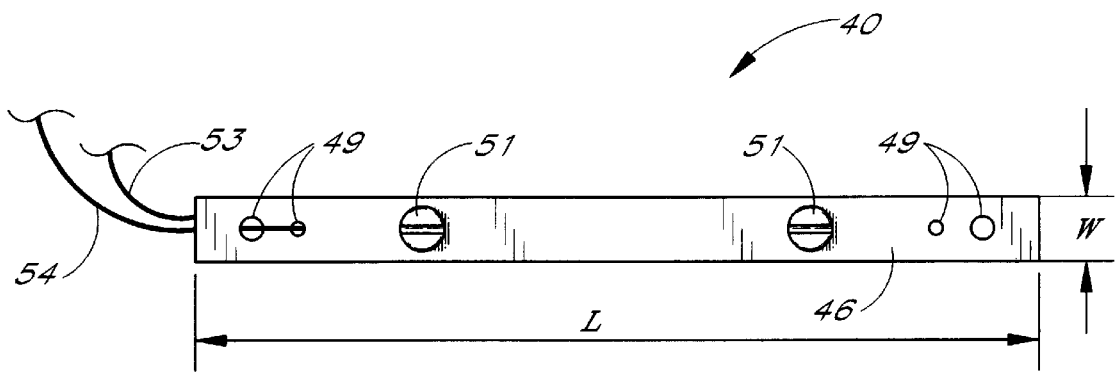
FIG. 3 is a side view of the moisture probe illustrated in FIG. 2.

FIGS. 2 and 3 illustrate a side view and top view, respectively, of a first embodiment of the moisture probe 40. It will be appreciated that, as used herein, the words "side" and "top" are with reference to the orientation depicted in enclosed drawings and are not intended to limit the scope of the invention. As shown in FIG. 2, the probe 40 includes two electrode plates 46. Preferably, each electrode plate 46 has an elongated, flat shape.

Advantageously, the width "W," length "L" and thickness "T" of opposing plates 46 are substantially the same. As shown, the electrode plates 46 are oriented in a predetermined spatial relationship relative to one another. Specifically, the electrode plates 46 are aligned in a substantially parallel relationship with the flat sides of the plates 46 facing each other, but separated by a distance D.

In the embodiment illustrated in FIG. 2, two cylindrically-shaped insulating spacers 50 are interposed between the electrode plates 46 to maintain the electrode plates 46 in the correct position relative to one another. A threaded fastener 51, such as a screw or bolt, (shown in phantom) extends axially through each of the spacers 50. The fasteners 51 and nuts 52 secure the spacers in between the electrode plates 46. The spacers 50, fasteners 51 and nuts 52 are preferably manufactured of a non-conductive, rigid material, such as plastic. Although illustrated in FIG. 2 as using two spacers 50, it will be appreciated by those skilled in the art that any wide number of spacers 50, having various shapes, may be used to maintain the distance and orientation between the electrode plates 46. Moreover, the spacers may be positioned at various points along the length of the electrode plates 46 and remain within the scope of the present invention. The spacers 50, however, are preferably small in diameter so they leave the space between plates 46 un-obstructed.

As shown in FIGS. 2 and 3, two electrically-conductive wires 53 and 54 are connected to each of the electrode plates 46. The wire 53 and 54 electrically connect the moisture probe 40 to the control unit 26. Referring to FIG. 3, the wires 53 and 54 communicate with the electrode plates 46 by extending through any number of apertures 49. Preferably, the wires 53 and 54 are threaded through adjacent apertures 49 before being fastened to the inside surface of the electrode plates 46 that face one another. This threading of wires 53, 54 through holes 49 strengthens the connection of the wires to the plates and protect the wires against detachment from the electrode plates 46.

The wires 53 and 54 may be secured to respective electrode plates 46 in a wide variety of well known manners, such as by soldering the wires 53, 54 to the electrode plates 46, or connecting the wires to screws through the plates, or other suitable electrical connections. The length of the wires 53 and 54 should be long enough to reach from the position of the control unit 26 to the location of the watering zone where the moisture probe 40 is located during use. The wires 53 and 54 are preferably encased in an insulating material to protect the wires from decay and to insulate them electrically from the surrounding environment.

Figure 4:
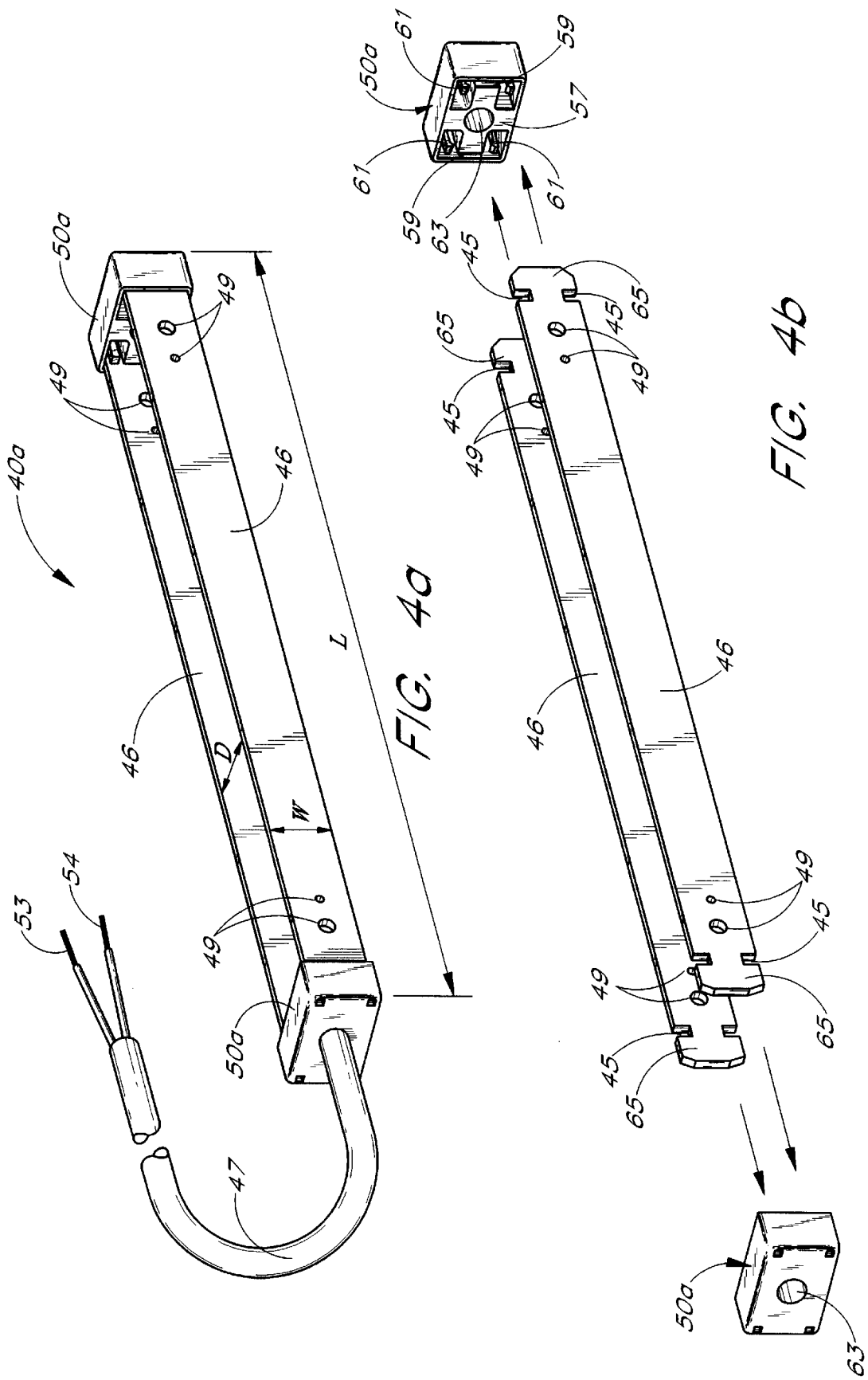
FIGS. 4a and 4b is are perspective views of a second embodiment of the moisture probe of the present invention.

FIG. 4a illustrates a second embodiment of the moisture probe, which is referred to herein as the moisture probe 40a. For ease of understanding, like reference numerals will be used between the two embodiments of the moisture probe. As shown in FIG. 4a, the moisture probe 40a includes two electrode plates 46 that are also aligned with the length L and width W of plates 46 parallel with respect to one another and separated by a distance D. The probe 40a also includes two insulating, spacers 50a which are located at opposite ends of the electrode plates 46. The spacers 50a function to maintain the electrode plates 46 in a fixed orientation relative to one another. A cable 47, which contains the electrical wires 53 and 54 extends from one of the spacers 50a. The wires 53 and 54 are threaded through apertures 49 in the electrode plates 46.

FIG. 4b illustrates the moisture probe 40a with the spacers 50a detached from the electrode plates 46. The spacers 50a are each rectangular shaped with an inner face 57 having opposed "U"-shaped apertures 59. Two tabs 61 are located in each U-shaped aperture 59. As discussed below, the U-shaped apertures 59 are sized to receive the ends of the electrode plates 46. A hole 63 extends through each of the spacers 50a. The hole 63 is sized to receive the cable 47 (FIG. 4a) for mounting the electrical wires 53 and 54 to the electrode plates 46.

As shown in FIG. 4b, a tongue 65 is located at each of the ends of the electrode plates 46. Notches 45 in the electrode plates 46 separates the tongue 65 from the main body of the electrode plate 46. Preferably, the tongues 65 are sized to be inserted into the U-shaped apertures 59, as illustrated by the arrows in FIG. 4b. Toward this end, the outer edges of the tongues 65 are preferably rounded to facilitate insertion of the tongues 65 into the U-shaped apertures 59. Preferably, notches 45 on the tongues 65 mate with the U-shaped apertures 59 in a snap-fit fashion, with the tabs 61 cooperating with the notches 45 to secure the tongues 59 within the spacers 50a.

The spacers 50a provides stability and rigidity to the shape of the probe 40a so that the parallel relationship between the electrode plates 46 is securely maintained. Because the spacers are mounted to the ends of the electrode plates 46, they advantageously do not obstruct the opening between the electrode plates 46 when the probe 40 is buried underground.

The dimensions of the moisture probe 40 may vary, as described below. The electrode plates 46 may range in length from about 5½ inches to 7 inches long. Preferably, the electrode plates 46 are about 5½ inches long, which exhibits optimal water detecting characteristics. The width of the electrode plates 46 may range from about ½ inch to 1½ inches. Preferably, the electrode plates 46 are each ½ inch wide. The electrode plates 46 may range in thickness from 1/16 inch to ¼ inch. Preferably, the electrode plates 46 are about 1/16 inch thick. The distance D between the electrode plates 46 may range from about 3/16 inch to about 1 inch, but are preferably from 3/16 inch to 7/16 inch. Preferably, the electrode plates 46 are spaced apart by a distance of about ½ inch. It is important that the electrode plates be maintained in a substantially parallel relationship. Preferably, a maximum deviation from parallel of no more than about ¼ inch is permitted.

The preferred dimensions of the probe 40 may also vary relative to one another rather than with respect to fixed dimensions. Thus, the electrode width is preferably approximately 8% to 20% of the electrode length. The thickness of the electrode plates 46 is preferably about 40% of the distance D between the electrode plates 46.

The electrode plates 46 are manufactured of an electrically conductive material, preferably high-purity copper, or a combination of various electrically-conductive materials. Electrode plates 46 made of a material consisting of 4% aluminum, 3% beryllium, 5% nickel, 5% tin, 2% lead and 2% zinc, with the remainder of the material consisting of copper, are believed suitable.

Figure 5:
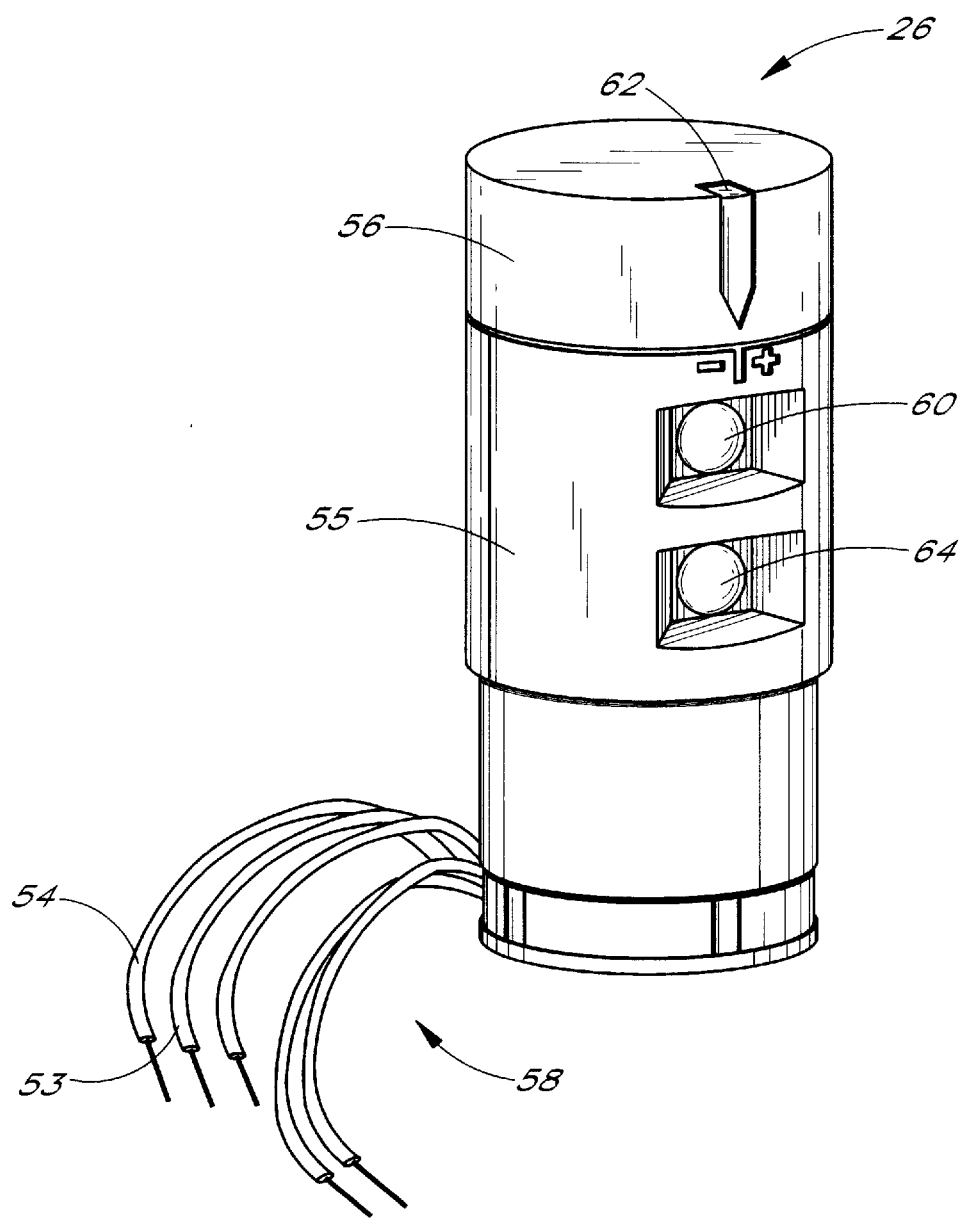
FIG. 5 is a perspective view of a preferred embodiment of a control unit that is used to control the sprinkler system of the present invention.

FIG. 5 illustrates the control unit 26. As shown, the control unit 26 includes a casing 55 that has a substantially cylindrical shape and houses the electronic components of the control unit 26. The control unit 26 also includes a rotatably mounted cap 56 that rotates in a direction normal to the longitudinal axis of the control unit 26. A plurality of electrical wires, including the wires 53 and 54, extend outward from the control unit 26 at the end opposite of the cap 56. The electrical wires 58 connect the control unit 26 to the various components of the irrigation system 20, such as the timer 22, the moisture probe 40, and the valve 30.

The control unit casing 55 encloses the photosensor 36 inside casing 55. Preferably, an aperture 60 extends through the casing 55 and communicates with the photosensor 36. The aperture 60 allows the passage of light into the casing 55 for detection by the photosensor 36. The aperture 60 is preferably covered by a transparent material, such as plastic, that allows light to pass into the control unit casing 55.

Referring to FIG. 5, the cap 56 is used as an adjuster to adjust the sensitivity of the moisture probe 40 in order to increase or decrease the moisture threshold at which the control unit enables or disables power to the irrigation system 20. As shown, the cap 56 includes a pointer 62 that points in the direction of the aperture 60 on the casing 55. The casing 55 includes a "+" sign and a "−" sign substantially adjacent one end of the cap 56. An operator may rotate the cap 56 to move the pointer 62 towards either the "+" sign or "−" sign on the casing 55 to thereby adjust the sensitivity of the moisture probe 40. Preferably, the operator rotates the pointer 62 towards the "+" sign in order to increase the moisture threshold at which the control unit disables power to the system. In other words, if an operator desires to allow more water to the watering zone, the operator moves the pointer 62 towards the "+" sign on the casing 55. It will be appreciated by those skilled in the art that the present invention is not limited to using a rotatable cap as the sensitivity adjuster. Any wide variety of methods may be used to vary the sensitivity of the moisture probe 40.

As shown in FIG. 5, the control unit 26 also includes an indicator light 64 for indicating the power status of the control unit 26. Preferably, the indicator light 64 illuminates in a variety of different colors, where a particular color corresponds to a particular power state of the control unit 26. For instance, the light 64 may be illuminated green to indicate that the timer 22 is allowing electrical power to pass to the control unit 26. An orange or amber light may indicate that the moisture probe 40 has detected low levels of moisture in the soil so that the controller energizes the valves 30.

Figure 6:
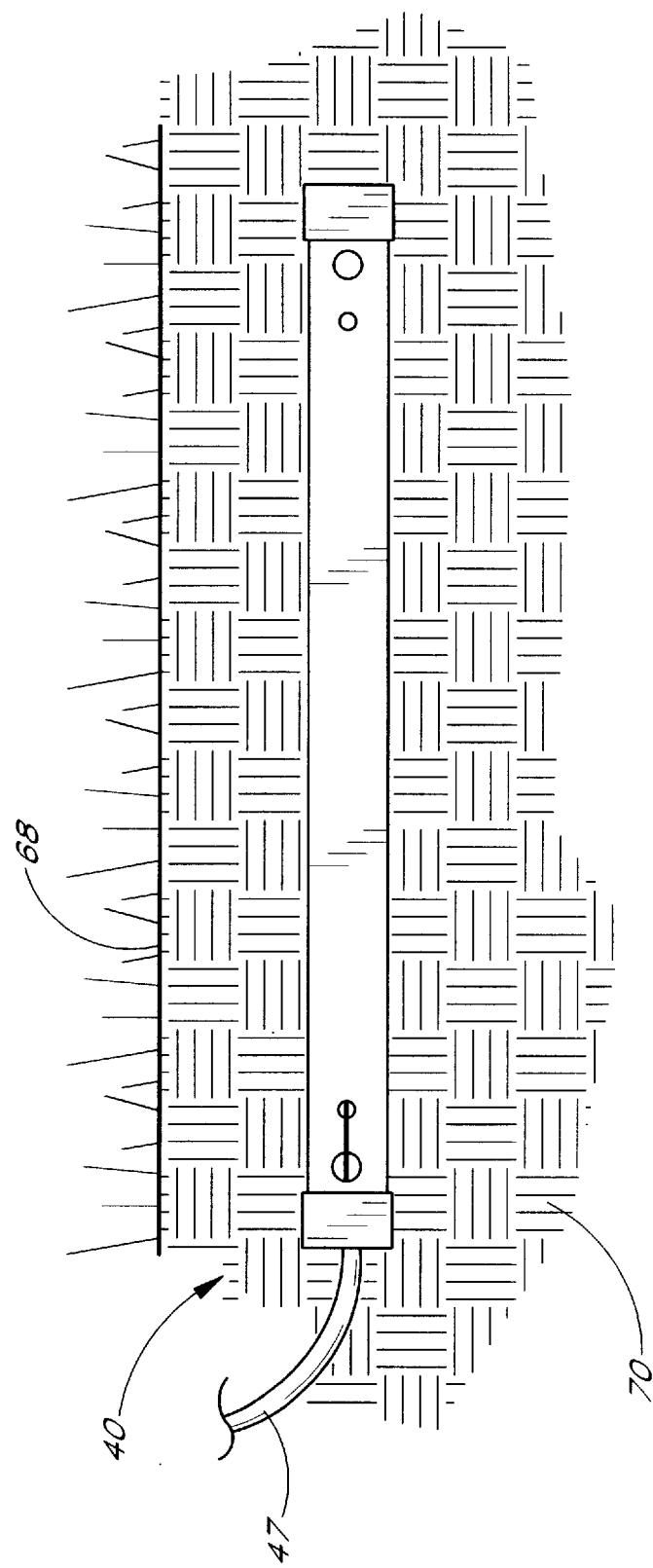
FIG. 6 is a side view of the moisture probe of FIG. 2 as positioned underground in a watering area.

FIG. 6 illustrates the preferred location and orientation of the control unit 40 during use. As shown, the moisture probe 40 is located in the watering zone below a ground level 68 so that the soil 70 in the watering zone surrounds the electrode plates 46. The probe 40 is preferably oriented with the space D between the electrode plates 46 open towards the ground level 68 and the length L of the plates 46 generally parallel to the ground level 68. This orientation allows water to flow downward from the ground level 68 and through the plates 46 of the probe 40, rather than accumulating on top of the electrode plates 46.

The probe 40 is preferably located at a depth suitable to detect the amount of moisture for the roots of the plants growing in the watering zone for which the moisture is to be controlled. In areas where the soil is covered by grass or small plants, the moisture probe should be buried at a depth of three to four inches to control the moisture to the grass or plants. If the watering zone includes trees that are to be watered, the moisture probe 40 should be buried at just below the shallowest tree roots, typically about 1 foot below ground level to control moisture to the trees. The probe 40 is preferably placed in any region of the watering area where the water disbursement range of the irrigation heads overlap. If the watering zone is sloped, the probe should be placed increasingly towards the top of the slope as the slope becomes steeper. Additionally, the probe 40 is preferably placed in the portion of the watering zone that receives the most sunlight.

Figure 7:
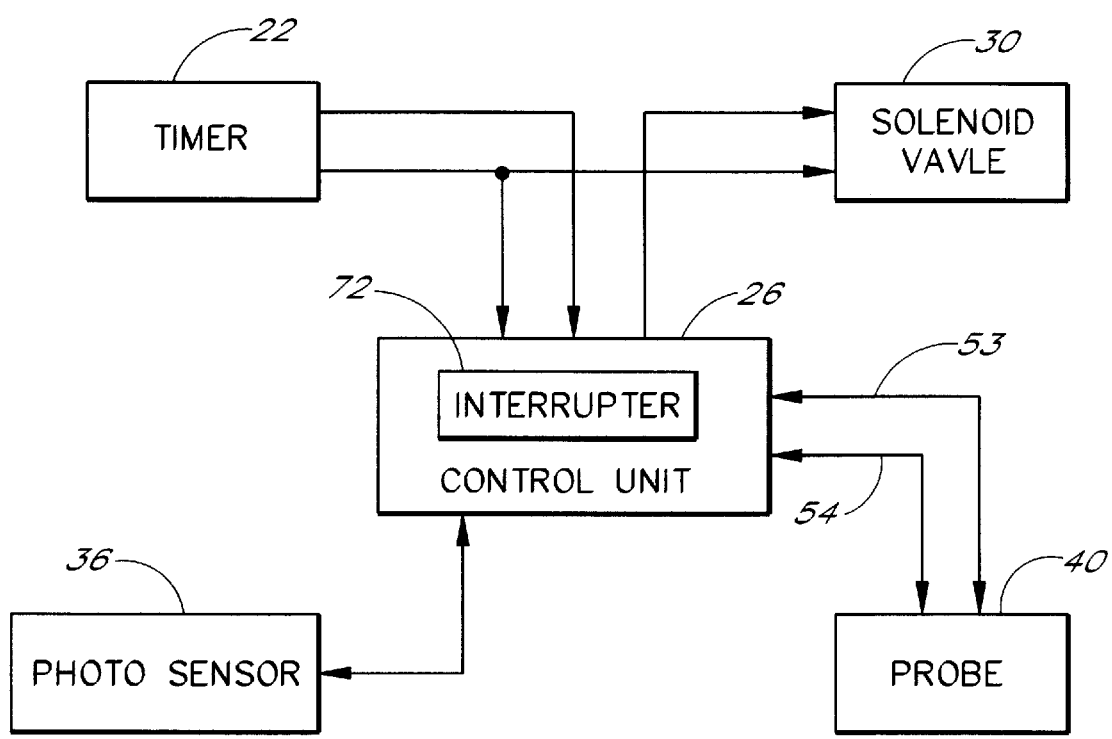
FIG. 7 is a block diagram of the sprinkler system of the present invention.

FIG. 7 is a block diagram that illustrates the operation of the irrigation system 20 in conjunction with the probe 40. At a predetermined time of day, the timer 22 enables electrical power to the control unit 26 and sends a corresponding signal to the control unit 26. The control unit then supplies electrical power to illuminate the indicator light 64 (FIG. 5) which notifies the user of the power status of the controller. The controller 26 also energizes the photosensor 36, if present. The photosensor 36 measures the level of light and sends a signal to the control unit 26 corresponding to whether light is above or below a predetermined threshold. If the light level is above a predetermined threshold value, then the control unit 26 activates an interrupter 72, which disables electrical power to the solenoid valve 30.

When power is received from the timer 22, the control unit 26 also applies an electricity to the impedance circuit formed by the electrode plates 46 of the moisture probe 40 through the wires 53, 54 to plates 46. Advantageously, a 1.5 volt direct current is applied to one of the probes 40, so there is a 1.5 volt potential between plates 46. The electrical resistance of the soil 70 that is located between the electrode plates 46 is a function of the level of moisture in the soil. If the soil contains a high level of moisture, the resistance exhibited by the soil is lower than if the soil contains a low moisture level. Accordingly, a higher resistance in the moisture probe 40 corresponds to a low moisture content in the watering zone. A relatively low resistance corresponds to a high moisture content. The moisture probe 40 then sends an electrical signal, having a voltage proportional to the resistance of the soil, to the control unit 26.

The control unit 26 enables or disables power to the valves 30 based upon the resistance of the soil as detected by the moisture probe 40. As discussed, the voltage of the signal sent by the probe 40 is proportional to the resistance as detected by probe 40 of the soil. The control unit 26, using a potentiometer, compares the resistance of the soil to a predetermined resistance value, corresponding to the resistance at which soil moisture is sufficient for the particular watering zone. As discussed above with reference to FIG. 5, an operator may manipulate the control unit 26 to adjust the predetermined resistance value. If the soil resistance is below the predetermined resistance value, then the moisture level is sufficiently high for the particular watering zone. The interrupter 72 in the control unit 26 then disables electrical power from being routed to the solenoid valve 30.

If the resistance measured by the moisture probe 40 rises above the predetermined value, the control unit 26 enables power to the valve 30 so that water is supplied to the irrigation heads 34 and the watering zone is watered. Preferably, the indicator light 64 (FIG. 5) on the control unit illuminates a predetermined color when the moisture level and light level are both sufficient such that the control unit routes electrical power to the valve 30.

The irrigation system 20 therefore does not irrigate the watering zone when the moisture level within the watering zone is above a predetermined value. The moisture probe 40 advantageously assists a user in conserving water by disabling irrigation to the watering zone unless the watering zone actually requires water. The probe 40 having the dimensions described herein advantageously exhibits optimal moisture detecting characteristics in a wide variety of soils so that minimum maintenance of the irrigation system 20 is required by a user. When used in combination with the timer 22 and the photosensor 36, the moisture probe 40 can be used to tailor irrigation of a watering zone to a variety of circumstances.

Figure 8:
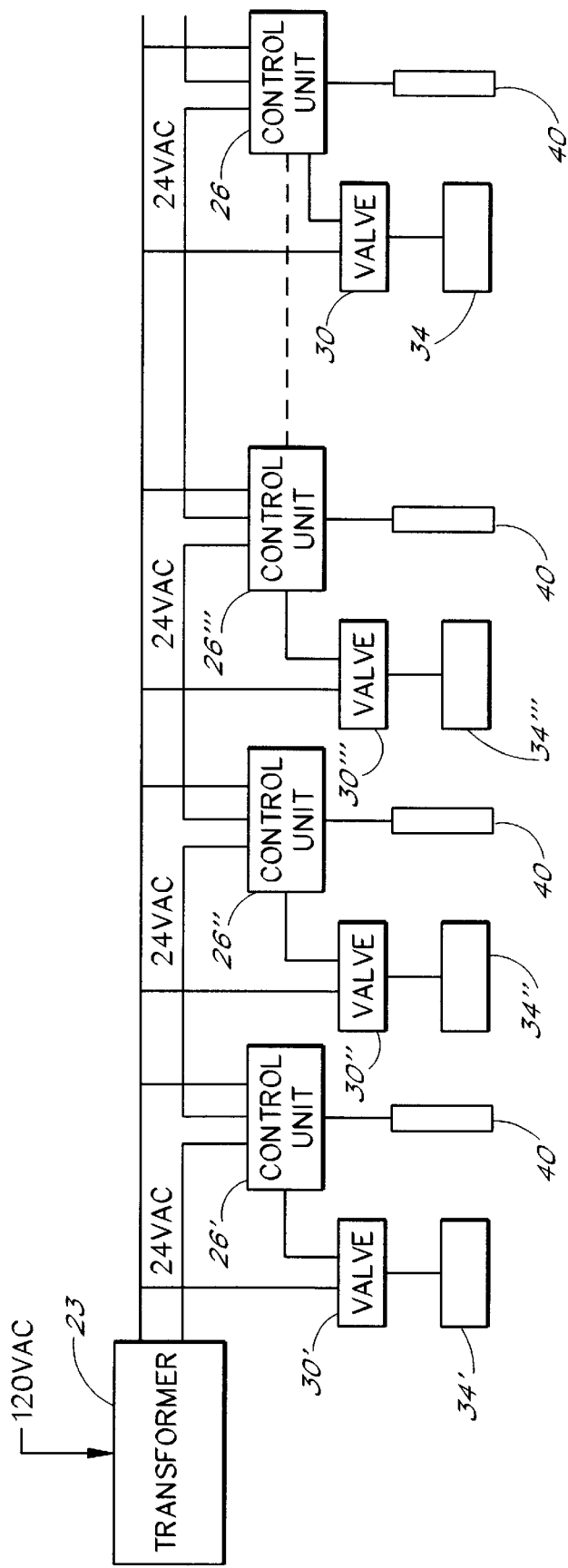
FIG. 8 is a schematic illustration of a sprinkler system having a series of moisture probes and control units.

As shown schematically in FIG. 8, the system 20 advantageously comprises a plurality of watering zones with one valve 30 and one head 34 for each watering zone. Further, there is advantageously a control unit 26 for each valve 30, with the various units 26 connected in series such that each valve 30 and its associated head 34 operate sequentially. This may be achieved, for example, by connecting a plurality of control units 26 in series, with each unit 26 having an open relay which is closed when the probe 40 associated with each unit 26 indicates that the moisture level in the soil is adequate. Thus, a first control unit 26' associated with a first valve 30' and a first watering zone is connected in series with a second control unit 26" associated with a second valve 30" and a second watering zone. The first control unit 26' contains an open relay that interrupts power to the second control unit 26". When the probe 40 associated with first control unit 26' indicates that the watering zone has sufficient moisture, then the relay is closed and power is supplied to the second control unit 26". The second control unit 26" contains an open relay that interrupts power to a third control unit 26'" until sufficient moisture is indicated by second probe 40" associated with the second control unit 26". The arrangement can be repeated as many times as desired, provided the wire connecting the units 26 is adequately sized.

Although the above description of the present invention has disclosed the features of the invention as applied to the various embodiments, it will be understood that various omissions, substitutions, and changes in the form of the detail of the embodiments illustrated may be made by those skilled in the art without departing from the spirit of the present invention. Consequently, the scope of the invention should not be limited to the foregoing disclosure.

What is claimed is:

1. A soil probe system configured to control the level of soil moisture in a watering area, comprising:

a first moisture probe including a first electrode having a substantially elongated, flat shape, said first electrode having a length, a width, and a thickness, a second electrode having a length, a width, and a thickness that are each substantially identical to said length, width, and thickness of said first electrode, said second electrode being oriented substantially aligned and parallel to said first electrode, said first electrode being spaced apart from said second electrode by a predetermined distance, and spacers removably connected to said first electrode and second electrode for maintaining the orientation of said first electrode relative to said second electrode when the electrodes are embedded in soil;

a source of electrical power connected to said first and second electrode for applying a first electrical potential to said first and second electrode;

a first control unit for measuring the electrical potential between said first and second electrode when said first and second electrodes are embedded in soil, said first control unit configured to disable a flow of electrical power from said source of electrical power to a first water valve if said first electrical potential is below a predetermined value.

2. The soil moisture probe of claim 1, wherein said length of said first electrode is within a range of about 5½ inches to 7 inches.

3. The soil moisture probe of claim 2, wherein said length of said first electrode is about 5½ inches.

4. The soil moisture probe of claim 2, wherein said thickness of said first electrode is within a range of $\frac{1}{16}$ inch to ¼ inch.

5. The soil moisture probe of claim 4, wherein said thickness of said first electrode is about $\frac{1}{16}$ inch.

6. The soil moisture probe of claim 4, wherein said width of said first electrode is within a range of $\frac{3}{16}$ inch to 1 inch.

7. The soil moisture probe of claim 6, wherein said width of said first electrode is about ½ inch.

8. The soil moisture probe of claim 6, wherein said predetermined distance is within a range of $\frac{3}{16}$ inch to 1 inch.

9. The soil moisture probe of claim 8, wherein said width of said first electrode is about ½ inch.

10. The soil moisture probe of claim 1, wherein a 24 volt potential is applied to said first and second electrodes.

11. The soil moisture probe of claim 1, wherein said first and second electrodes are each manufactured of a material consisting of about 4% aluminum, 3% beryllium, 5% nickel, 5% tin, 2% lead and 2% zinc, with the majority of the remaining material consisting of copper.

12. The soil moisture probe system of claim 1, wherein said spacers are removably mounted to opposite ends of said first and second electrodes.

13. The soil moisture probe system of claim 12, wherein said spacers contain apertures sized to receive ends of said first and second electrodes such that said spacers mount to said first and second electrodes in a snap-fit fashion.

14. The soil moisture probe system of claim 1, wherein said spacers are interposed between said first and second electrodes.

15. The soil probe system of claim 1, wherein said first moisture probe is located in a first watering zone along a power path connecting the source of electrical power to the first moisture probe.

16. The soil probe system of claim 15, additionally comprising:

a second moisture probe including a third electrode having a substantially elongated, flat shape, said third electrode having a length, a width, and a thickness, a fourth electrode having a length, a width, and a thickness that are each substantially identical to said length, width, and thickness of said third electrode, said fourth electrode being oriented substantially aligned and parallel to said third electrode, said fourth electrode being spaced apart from said third electrode by a predetermined distance, and spacers removably connected to said third and fourth electrodes for maintaining the orientation of said third electrode relative to said fourth electrode, wherein said second moisture probe is located along said power path in a second watering zone so that said source of electrical power applies a second electrical potential to said third and fourth electrodes;

a second control unit for measuring the electrical potential between said third and fourth electrode, said second control unit configured to disable a flow of electrical power from said source of electrical power to a second water valve if said second electrical potential is below a predetermined value; and a relay located in said power path between said source of electrical power and said second moisture probe, said relay controlled by said first control unit to allow power to flow across said relay to said second control unit and said second moisture probe when the moisture level in the first watering zone is greater than or equal to a predetermined level, and to inhibit power from passing across said relay when the moisture level in the first watering zone less than a predetermined level.

17. A watering system for watering a series of soil watering zones comprising:

a power supply for supplying power along a power path;

a first soil probe system located along said power path and including a first water valve connected to a first sprinkler, a first soil moisture probe configured to measure the moisture level in a first soil watering zone, and a first control unit communicating with said first moisture probe and said first water valve, said first control unit configured to close the first water valve if said soil moisture level is below a predetermined level;

a second soil probe system located along said power path, said second soil probe system including a second water valve connected to a second sprinkler, a second moisture probe configured to measure the moisture level in a second soil watering zone, and a second control unit configured to close the second water valve if the moisture level in the second soil watering zone is below said predetermined level;

a relay located in said power path between said power supply and said second soil probe system, said relay controlled by said first control system to allow power to flow across said relay to said second soil probe system when the moisture level in the first soil watering zone is greater than or equal to said predetermined level, and to inhibit power from passing across said relay when the moisture level in the first zone watering zone less than the predetermined level;

wherein the first and second moisture probes each comprise a first electrode having a substantially elongated, flat shape, said first electrode having a length, a width, and a thickness, a second electrode having a length, a width, and a thickness that are each substantially identical to said length, width, and thickness of said first electrode, said second electrode being oriented substantially aligned and parallel to said first electrode, said first electrode being space apart from said second electrode by a predetermined distance, and spacers removably connected to said first electrode and second electrode for maintaining the orientation of said first electrode relative to said second electrode.

18. The soil moisture probe of claim 17, wherein said length of said first electrode is within a range of about 5½ inches to 7 inches.

19. The soil moisture probe of claim 18, wherein said length of said first electrode is about 5½ inches.

20. The soil moisture probe of claim 17, wherein said thickness of said first electrode is within a range of $1/16$ inch to ¼ inch.

21. The soil moisture probe of claim 20, wherein said thickness of said first electrode is about $1/16$ inch.

22. The soil moisture probe of claim 21, wherein said width of said first electrode is within a range of $3/16$ inch to 1 inch.

23. The soil moisture probe of claim 22, wherein said width of said first electrode is about ½ inch.

24. The soil moisture probe of claim 22, wherein said predetermined distance is within a range of $3/16$ inch to 1 inch.

25. The soil moisture probe of claim 24, wherein said width of said first electrode is about ½ inch.

26. The soil moisture probe of claim 17, wherein said first and second electrodes are each manufactured of a material consisting of about 4% aluminum, 3% beryllium, 5% nickel, 5% tin, 2% lead and 2% zinc, with the majority of the remaining material consisting of copper.

* * * * *